United States Patent [19]

Noiles et al.

[11] 4,407,286

[45] Oct. 4, 1983

[54] SURGICAL STAPLES

[75] Inventors: Douglas G. Noiles, New Canaan; John O. Crawford, Brookfield Center, both of Conn.

[73] Assignee: United States Surgical Corporation, Norwalk, Conn.

[21] Appl. No.: 377,860

[22] Filed: May 13, 1982

Related U.S. Application Data

[63] Continuation of Ser. No. 181,092, Aug. 25, 1980, abandoned.

[51] Int. Cl.³ .............................................. A61B 17/04
[52] U.S. Cl. ................... 128/334 R; 128/337; 227/83; 227/DIG. 1; 411/457
[58] Field of Search ................... 128/334 R, 337, 336; 411/456, 451, 457, 470–476, 490, 497, 487, 469; 227/83, DIG. 1, 19

[56] References Cited

U.S. PATENT DOCUMENTS

| Re. 28,932 | 8/1976 | Noiles et al. | 227/19 |
|---|---|---|---|
| 274,481 | 3/1883 | Frost | 411/471 |
| 506,861 | 10/1893 | Prentice . | |
| 517,836 | 4/1894 | Bradish | 411/472 X |
| 816,026 | 3/1906 | Meier . | |
| 1,199,653 | 9/1916 | Bacolini . | |
| 1,910,688 | 5/1933 | Goodstein . | |
| 1,945,377 | 1/1934 | Posnack | 1/49 |
| 2,008,086 | 7/1935 | Sorenson | 85/49 |
| 2,351,608 | 6/1944 | Greenwood | 59/77 |
| 2,526,902 | 10/1950 | Rublee | 411/471 X |
| 3,077,812 | 2/1963 | Dietrich | 85/49 |
| 3,086,208 | 4/1963 | Eby | 1/56 |
| 3,638,847 | 2/1972 | Noiles et al. | 277/120 |
| 3,643,851 | 2/1972 | Green et al. | 227/19 |
| 3,650,453 | 3/1972 | Smith, Jr. | 227/138 |
| 3,662,939 | 5/1972 | Bryan | 227/19 |
| 3,713,533 | 1/1973 | Reimels | 206/56 DF |
| 3,717,294 | 2/1973 | Green | 227/19 |
| 3,837,555 | 9/1974 | Green | 227/130 |
| 3,869,957 | 3/1975 | Barth et al. | 85/49 |
| 4,014,492 | 3/1977 | Rothfuss | 227/19 |
| 4,043,504 | 8/1977 | Hueil et al. | 227/116 |
| 4,109,844 | 8/1978 | Becht | 227/120 |
| 4,166,466 | 9/1979 | Jarvik | 128/325 |
| 4,179,057 | 12/1979 | Becht et al. | 227/19 |
| 4,196,836 | 4/1980 | Becht | 227/110 |
| 4,202,480 | 5/1980 | Annett | 227/8 |

FOREIGN PATENT DOCUMENTS

| 342781 | 1/1960 | Switzerland | 411/470 |
|---|---|---|---|
| 737897 | 10/1955 | United Kingdom | 411/476 |
| 855647 | 12/1960 | United Kingdom . | |

Primary Examiner—Michael H. Thaler
Attorney, Agent, or Firm—Robert R. Jackson; John E. Nathan

[57] ABSTRACT

A surgical staple of the type which is applied by being bent around an anvil in a surgical stapler has two spaced surfaces transverse to the longitudinal axis of the staple and located so that when the staple is bent around the anvil, the transverse surfaces cooperate with the anvil to prevent the staple from being pulled back into the stapler.

8 Claims, 8 Drawing Figures

U.S. Patent    Oct. 4, 1983    Sheet 1 of 2    4,407,286
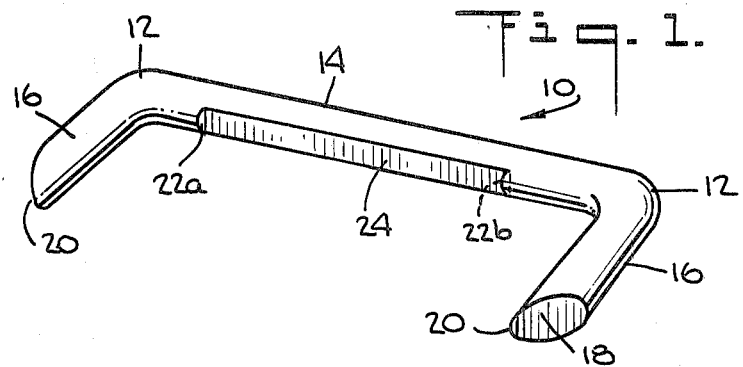
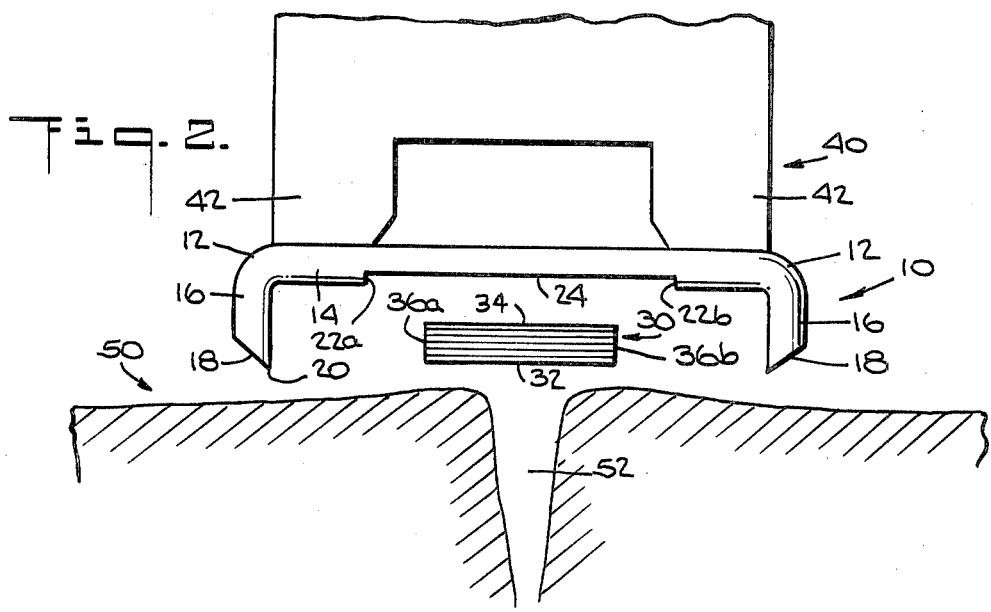
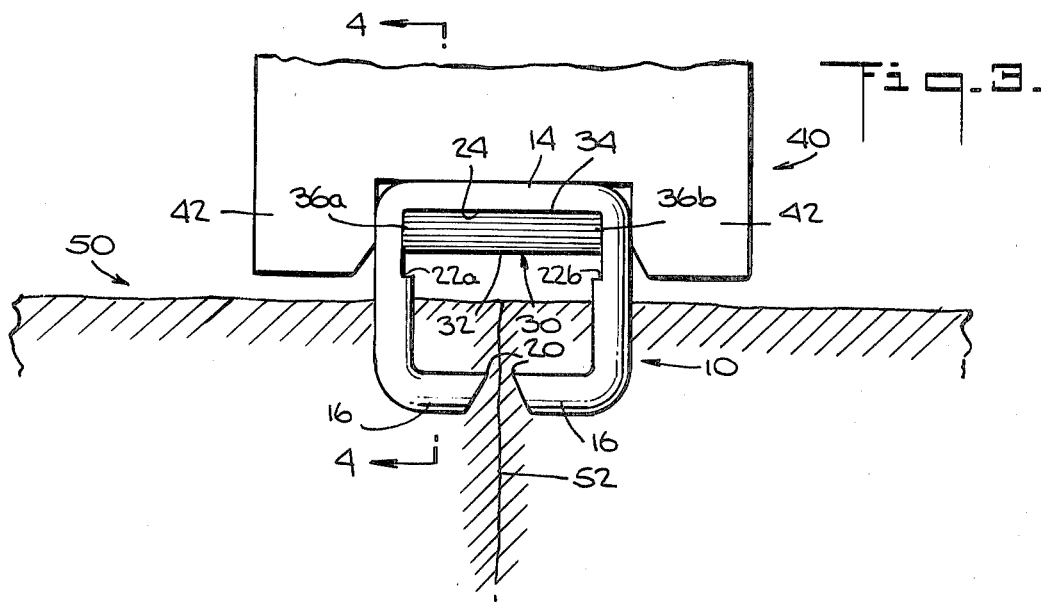

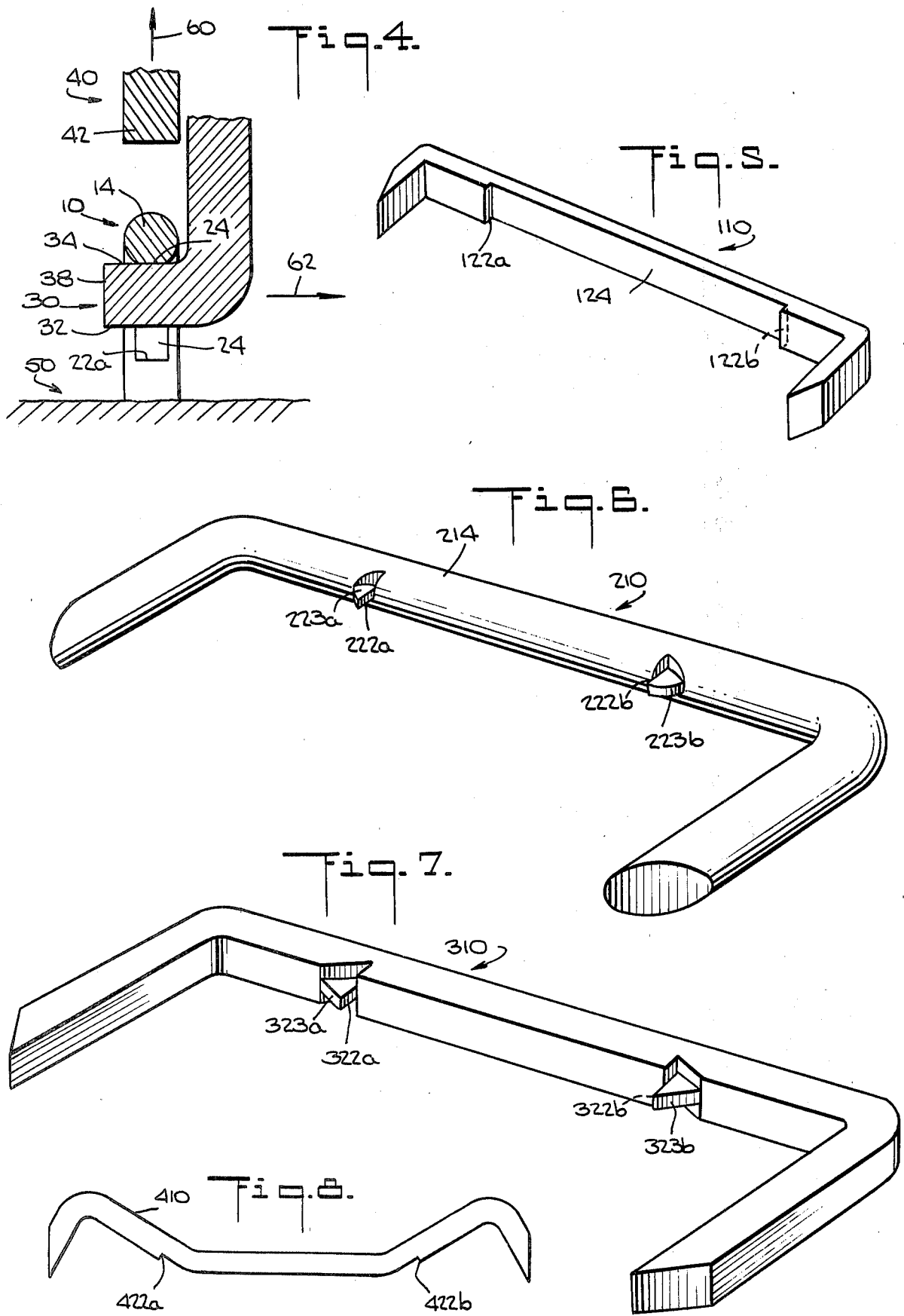

SURGICAL STAPLES

This is a continuation of application Ser. No. 181,092, filed Aug. 25, 1980, now abandoned.

BACKGROUND OF THE INVENTION

This invention relates to surgical staples, and more particularly to surgical staples of the type which are formed around an anvil in a surgical stapler.

Surgical stapling apparatus for applying staples to close incisions or wounds in body tissue are shown, for example, in Green et al. U.S. Pat. Nos. 3,643,851, Smith 3,650,453, and Green 3,837,555. In these devices, a surgical staple which is typically preformed in a broad-based, square-cornered U shape is advanced toward an anvil by a staple pusher having an end with a generally U-shaped recess. The base of the U-shaped recess in the staple pusher is broader than the anvil, but not as broad as the base of the U-shaped staple. When the staple reaches the anvil, the staple pusher causes the staple to bend around the anvil into a closed, square-cornered C shape. (In this specification and in the appended claims, this is referred to as forming the staple.) As this is taking place, the ends of the staple enter the tissue on the respective opposite sides of the incision or wound and draw the tissue together. When the staple has been fully formed, the staple pusher is retracted and the stapler is removed by sliding the anvil out from within the staple. The staple remains in the tissue to hold it together during healing.

Occasionally in surgical staplers of the type described above, the staple may not readily release from the U-shaped recess in the staple pusher after the staple has been formed and the staple pusher is being retracted. This may be because of residual stresses in the staple which cause it to press against the sides of the staple pusher recess in a spring-like fashion. When this occurs, the formed staple tends to be pulled back into the stapler, with the possible consequences of injury to the tissue being stapled and difficulty in freeing the stapler from the staple.

One solution which has been found to this occasional problem is to design the stapler so that the fit between the staple pusher, the staple, and the anvil is relatively loose, with the degree of looseness being carefully selected and controlled to minimize the instances in which the staple pusher fails to readily release the staple. Achieving and maintaining just the right degree of looseness in the design of the stapler, however, requires extremely precise manufacturing tolerances, thereby increasing the cost of the stapler. This relatively loose design may also produce finished staples which are not as neatly and regularly formed as would be most desirable. It may also contribute to other possible operating problems in the stapler, such as allowing a staple to occasionally roll, twist, or slip off the anvil during formation, with the result that the staple is improperly or incompletely formed or not formed at all. These problems of rolling, twisting, and slipping are most likely to occur with staples made of round wire, which is the most common and generally the preferred surgical staple stock.

In view of the foregoing, it is an object of this invention to provide improved surgical staples of the type which are formed by being bent around an anvil.

It is a more particular object of this invention to provide improved surgical staples of this type which are not subject to being pulled back into the stapler when the staple pusher is retracted, and which may also have reduced tendency to roll, twist, or slip off the anvil during formation.

SUMMARY OF THE INVENTION

These and other objects of the invention are accomplished in accordance with the principles of the invention by providing a surgical staple with two spaced surfaces transverse to the longitudinal axis of the staple and located on the staple so that when the staple is formed around the anvil, these transverse surfaces cooperate with the anvil to prevent the staple from being pulled back into the stapler when the staple pusher is retracted. The improved staples of this invention allow the staplers with which they are used to be designed so that there is a tighter fit among the staple pusher, staple, and anvil. This eases manufacturing tolerances, reduces manufacturing cost, produces more neatly formed staples, and reduces the possibility that a staple may roll, twist, or slip off the anvil during formation. To further reduce the possibility of staple roll, twist, or slip, particularly with staples made of round wire, the portion of the side surface of the staple which contacts the anvil may be made flat to help stabilize the staple on the anvil during staple formation.

Further features of the invention, its nature and various advantages will be more apparent from the accompanying drawing and the following detailed description of the invention.

BRIEF DESCRIPTION OF THE DRAWING

FIG. 1 is a perspective view of an illustrative embodiment of the improved surgical staple of this invention.

FIG. 2 is another view of the staple of FIG. 1 in use in conjunction with illustrative surgical stapler apparatus.

FIG. 3 shows the apparatus of FIG. 2 after the staple has been fully formed by the stapler.

FIG. 4 is a sectional view taken along the line 4—4 in FIG. 3 showing how the stapler apparatus is removed from the finished staple.

FIG. 5 is a perspective view of another illustrative embodiment of the improved surgical staple of this invention.

FIG. 6 is a perspective view of another illustrative embodiment of the improved surgical staple of this invention.

FIG. 7 is a perspective view of yet another illustrative embodiment of the improved surgical staple of this invention.

FIG. 8 is an elevational view of still another illustrative embodiment of the improved surgical staple of this invention.

DETAILED DESCRIPTION OF THE INVENTION

An illustrative embodiment of the surgical staple of this invention is shown prior to formation in a stapler in FIGS. 1 and 2. As shown in these Figures, illustrative staple 10 is made of metal wire having initially round cross section. The staple is preformed into a broad-based U or channel shape with relatively sharp corners 12. The base of the staple is designated 14, and the parallel legs of the staple are designated 16. The ends 18 of legs 16 opposite base 14 are cut off at an angle to provide sharp tips 20 for allowing the staple to more easily and cleanly enter the tissue. Typical material for staple 10 is 316-L stainless steel wire having a diameter of 0.020 or 0.022 inches. Other materials and sizes are, of course, well known to those skilled in the art.

In accordance with the present invention, staple 10 is preformed with two spaces surfaces 22a and 22b on staple base 14 transverse to the longitudinal axis of the staple base and located on the side of the staple base which initially contacts anvil 30 in a stapler as described below. In the particular embodiment shown in FIGS. 1 and 2, transverse surfaces 22a and 22b are the opposite ends of a recessed portion 24 of the side surface of staple base 14. Recessed surface 24 is located centrally between staple legs 16 so that transverse surfaces 22a and 22b are located symmetrically about the midpoint of staple base 14. The considerations governing the spacing of surfaces 22a and 22b are discussed in detail below.

Recessed surface 24 may be formed in the staple in any of a number of ways to produce transverse surfaces 22a and 22b. For example, surface 24 may be formed by coining, milling, shaving, or broaching the staple. Although in the particular embodiment shown in FIGS. 1 and 2, surfaces 22a and 22b are substantially perpendicular to the longitudinal axis of staple base 14, this is not necessarily the case, and the term "transverse" as applied to such surfaces is used herein and in the appended claims to mean a surface forming a substantial angle with the longitudinal axis of the adjacent portion of the staple and capable of performing the functions described in detail below. The considerations governing the dimensions of surfaces 22a and 22b are discussed in detail below. For present purposes, however, it will be sufficient to indicate that for staples having diameter of 0.020 or 0.022 inches, surface 24 may be recessed approximately 0.002 inches so that the maximum dimension of surfaces 22a and 22b measured perpendicular to surface 24 is about 0.002 inches.

Although recessed surface 24 is preferably flat as shown in FIGS. 1 and 2 for reasons discussed in detail below, this is not required, and surface 24 may have any shape which will produce suitable transverse surfaces 22a and 22b at its respective opposite ends.

In use in a surgical stapler as shown in FIGS. 2 and 3, staple 10 is advanced toward anvil 30 by staple pusher 40, both of which are part of the stapler (not otherwise shown in the drawing). The stapler may be a conventional instrument of the type shown, for example, in Green et al. U.S. Pat. No. 3,643,851, and it may be used in the conventional way. Assuming for purposes of illustration that the stapler is a skin stapler, the stapler is held as shown in FIG. 2 so that the distal side 32 of anvil 30 is adjacent the skin tissue 50 to be stapled and so that one of staple legs 16 is on each side of the incision or wound 52 to be closed. The staple is oriented in the stapler so that the sharp ends 20 of staple legs 16 point toward the tissue to be stapled. The staple is aligned in the stapler so that it is located symmetrically relative to anvil 30. This orientation and alignment of the staple causes recessed surface 24 of the staple to face the proximal side 34 of anvil 30, with transverse surfaces 22a and 22b being respectively spaced at equal distances from the adjacent lateral sides 36a and 36b of the anvil.

As staple pusher 40 advances staple 10 toward anvil 30, the central portion of recessed surface 24 initially contacts proximal side 34 of anvil 30. The ends 20 of staple legs 16 also being to penetrate the tissue. Thereafter, as staple pusher 40 continues to advance, the distal ends 42 of staple pusher 40 bend the portions of staple base 14 which extend beyond the distal side of anvil 30 around the anvil until those portions of the staple base are substantially parallel to one another and substantially perpendicular to the remaining central portion of the staple base as shown in FIG. 3. As this occurs, staple legs 16 further penetrate the tissue, are reoriented toward one another, and, in cooperation with the portions of the staple base which enter the tissue, draw the tissue on the two sides of incision or wound 52 together, as is also shown in FIG. 3. Formation of the staple is now complete.

It will be noted in FIG. 3 that when the staple has been fully formed as shown, transverse surfaces 22a and 22b are adjacent the respective opposite ends of the distal side 32 of anvil 30. When staple pusher 40 is retracted to release the staple from the stapler, these surfaces will contact the ends of distal side 32 to substantially prevent the staple from moving transversely of laterally of the anvil in the direction opposite the direction in which the staple was advanced toward the anvil. In particular, transverse surfaces 22a and 22b cooperate with the distal side of anvil 30 to pull the staple from the recessed end of the staple pusher in the event that the staple pusher does not otherwise readily release the staple. In this way transverse surfaces 22a and 22b cooperate with anvil 30 to prevent the staple pusher from pulling the staple back into the stapler when the staple pusher is retracted.

In order to have transverse surfaces 22a and 22b properly located relative to the distal side 32 of anvil 30 when the staple has been fully formed, the initial spacing of transverse surfaces 22a and 22b must be at least slightly greater than the portion of the periphery of the anvil cross section immediately adjacent the finished staple, i.e., the portion of the anvil periphery excluding distal side 32. For example, in the case of a stapler for use with an anvil 30 of rectangular cross section as shown in FIGS. 2 and 3, the initial spacing of transverse surfaces 22a and 22b is preferably equal to the width of the anvil, plus twice the thickness of the anvil, plus a small clearance (e.g., approximately 0.01 inches in the case of staples with the specific dimensions mentioned above). This clearance must be large enough to compensate for any shortening of the inside surface 24 of the staple due to bending of staple base 14 during staple formation.

In order for transverse surfaces 22a and 22b to cooperate with the distal side 32 of anvil 30 as described above, transverse surfaces 22a and 22b must be at least prominent enough to overlap the ends of distal side 32 when the staple has been fully formed. The important dimension of transverse surfaces 22a and 22b for this purpose is the amount by which these surfaces project from the staple surface between them (i.e., surface 24 in the illustrative embodiment being described). The required amount of this projection will depend on several factors such as the overall size of the staple and the closeness of the staple to the lateral sides 36a and 36b of the anvil when the staple is fully formed around the anvil. In the case of staples with the specific dimensions mentioned above, it has been found that transverse surfaces 22a and 22b projecting about 0.002 inches outward from recessed surfaces 24 give good results.

FIG. 4 shows how the stapler is removed after the staple has been fully formed. First, staple pusher 40 is retracted as indicated by arrow 60. Thereafter, anvil 30 is slipped out of the staple by moving it in the direction of arrow 62. The staple typically remains in the tissue during healing of the incision or wound, after which the staple may be removed by other conventional means.

The presence of transverse surfaces 22a and 22b to help prevent the staples from being pulled back into the stapler when staple pusher 40 is retracted makes the design of all components of the system (i.e., staple 10, anvil 30, and staple pusher 40) less critical than would otherwise be necessary to minimize the possibility of this type of malfunction. The anvil and staple pusher can be made to form the staple much more closely around the anvil without increasing the possibility that a staple may not release from the staple pusher when it retracts. This produces staples which are more perfectly, uniformly, and neatly formed. It is no longer as critical to maintain the precise degree of looseness between the staple, anvil, and staple pusher which is otherwise desirable to promote release of the fully formed stales from the staple pusher without loss of control of the staples during formation. This eases manufacturing tolerances on the staples and the stapler, thereby facilitating manufacture, reducing costs, and enhancing reliability.

The staple shown in FIGS. 1-4 and described above has other advantages which have not yet been discussed. The presence of substantially flat recessed surface 24 on the side of the staple which contacts anvil 30 stabilizes the staple on the anvil while it is being formed. This reduces the possibility that a staple may roll or twist on the anvil as it is being forced into the tissue and formed around the anvil. It also reduces the possibility that a staple may slip off the end 38 (FIG. 4) of the anvil before it has been fully formed and the stapler is being deliberately removed from the staple. Thus, although the staple is basically a round wire staple as is most common and also frequently preferred, it has a relatively small flat surface 24 which contributes substantially to its stability during formation by the stapler and thereby enhances the reliability of the apparatus.

Although in the embodiment shown in FIGS. 1-4 the staple is round wire and transverse surfaces 22a and 22b are the opposite ends of a recessed portion of the side surface of the staple, the staples of this invention may have many other cross sectional shapes and the transverse surfaces may be formed in many other ways. In FIG. 5, for example, staple 110 has a flat or rectangular cross section and transverse surfaces 122a and 122b are formed as the respective opposite ends of recess 124. In other respects staple 110 is similar to staple 10 and may be used in the same way.

In the alternative embodiment shown in FIG. 6, staple 210 is again made of round wire, but transverse surfaces 222a and 222b are the facing surfaces of two spaced projections or barbs 223a and 223b on staple base 214. These barbs may have any of a wide variety of shapes and may be formed in any of a wide variety of ways. For example, barbs 223a and 223b may be formed by staking or pinching the wire of the staple and thereby raising the barbs. In other respects staple 210 may be similar to the previously described embodiments, although it does not have a flat surface for cooperating with a flat anvil surface to increase the stability of the staple on the anvil during staple forming as described above in connection with FIGS. 1-4.

Staple 310 in FIG. 7 is similar to staple 210 except that the staple is made of square wire. As in the case of staple 210, transverse surfaces 322a and 322b are the facing surfaces of barbs 323a and 323b, respectively.

The invention is not limited in its application to surgical staples having an initially square-cornered U or channel shape, but is equally applicable to surgical staples having many other starting shapes. For example, FIG. 8 shows a staple 410 of the type shown in Rothfuss U.S. Pat. No. 4,014,492 but modified in accordance with the principles of the present invention to include transverse surfaces 422a and 422b for cooperating with the anvil in the Rothfuss apparatus in the same way that surfaces 22a and 22b cooperate with anvil 30 in the apparatus of FIGS. 2-4 above.

It will be understood that the embodiments shown and described herein are merely illustrative of the principles of the invention, and that various modifications can be made by those skilled in the art without departing from the scope and spirit of the invention. For example, the staple can be made with any of a wide variety of cross sectional shapes as described above.

We claim:

1. The method of applying surgical staples to body tissue comprising the steps of:

positioning an anvil member adjacent to the surface of the tissue to be stapled;

providing a surgical staple having a longitudinal base, two legs at respective opposite ends of the base, and two surfaces on the base transverse to the longitudinal axis of the base, the transverse surfaces facing one another and being spaced longitudinally along the base from one another and from the legs;

positioning the staple so that the base is substantially parallel to the surface of the tissue to be stapled and so that a central portion of the base intermediate the transverse surfaces is in contact with an anvil member surface which faces away from the surface of the tissue;

advancing a staple former substantially perpendicular to the surface of the tissue to bend the staple base around the anvil member so that the legs of the staple penetrate the tissue and so that the transverse surfaces overlap portions of the anvil member surface which face the surface of the tissue to substantially prevent retraction of the staple by the staple former when the staple former is subsequently retracted in a direction opposite the staple former advancing direction; and retracting the staple former in the direction opposite the staple former advancing direction to leave the formed staple around the anvil member and in the tissue.

2. The method of claim 1 further comprising the step of removing the anvil from within the formed staple.

3. Surgical stapling apparatus for applying surgical staples to body tissue comprising:

anvil means for providing a structure around which a staple is formed during application of the staple to the tissue, the anvil means including first and second spaced surface portions that face the surface of the tissue to be stapled during application of the staple to the tissue;

a surgical staple having a longitudinal base and two legs located at respective opposite ends of the base, the base including first and second surfaces transverse to the longitudinal axis of the base, the first and second transverse surfaces facing one another and being spaced longitudinally along the base from one another and from the legs; and staple pusher means for advancing the staple into contact with the anvil means intermediate the first and second transverse surfaces and for bending the base of the staple intermediate the first and second transverse surfaces around the anvil means so that the legs of the staple penetrate the tissue and so that the first and second transverse surfaces respectively overlap the first and second anvil surfaces to substantially prevent the staple from being pulled back with the staple pusher means when the staple pusher means is retracted.

4. The apparatus defined in claim 3 wherein the first and second transverse surfaces are spaced apart by a distance equal to the sum of (1) the portion of the periphery of the anvil means immediately adjacent to the staple when the staple is bent around the anvil means and (2) a clearance dimension.

5. The apparatus defined in claim 3 wherein the anvil means has a rectangular cross section in the plane in which the staple is bent around the anvil means, and wherein the spacing between the first and second transverse surfaces is equal to the sum of (1) the width and twice the thickness of the rectangular cross section of the anvil means and (2) a clearance.

6. The apparatus defined in claim 3 wherein the first and second transverse surfaces are the respective opposite ends of a single continuous recessed portion of the surface of the base.

7. The apparatus defined in claim 6 wherein the recessed portion of the surface of the base is substantially flat before the staple is bent around the anvil means.

8. The apparatus defined in claim 3 wherein each of the first and second transverse surfaces is a portion of the surface of respective first and second projections extending outward from the side of the base.

* * * * *